(12) United States Patent
Kilgore

(10) Patent No.: US 6,183,428 B1
(45) Date of Patent: *Feb. 6, 2001

(54) VIBRATING TAMPON APPARATUS

(76) Inventor: Steven A. Kilgore, 910 Ward Run, Raymore, MO (US) 64083

( * ) Notice: Under 35 U.S.C. 154(b), the term of this patent shall be extended for 0 days.

This patent is subject to a terminal disclaimer.

(21) Appl. No.: 09/304,045
(22) Filed: May 4, 1999
(51) Int. Cl.⁷ ...................................................... A61H 21/00
(52) U.S. Cl. ................................ 601/70; 601/72; 604/904
(58) Field of Search .................................. 601/46, 47, 69, 601/70, 71, 72, 78, 80, 81; 604/904, 363

(56) References Cited

U.S. PATENT DOCUMENTS

| 2,422,639 | * | 6/1947 | Wenander | 601/46 |
| 3,626,931 | * | 12/1971 | Bysakh | 601/46 |
| 3,669,100 | * | 6/1972 | Csanad | 601/46 |
| 4,007,735 | * | 2/1977 | Magnusson | 601/75 |
| 4,515,167 | * | 5/1985 | Hochman | 600/549 |
| 5,067,480 | * | 11/1991 | Woog et al. | 601/46 |
| 5,072,724 | * | 12/1991 | Marcus | 601/46 |
| 5,782,745 | * | 7/1998 | Benderev | 600/60 |
| 5,782,779 | | 7/1998 | Kilgore | 601/70 |

* cited by examiner

Primary Examiner—Justine R. Yu
(74) Attorney, Agent, or Firm—Henderson & Sturm LLP

(57) ABSTRACT

An improved vibrating tampon apparatus 10 for easing a woman's menstrual cramps; wherein, the apparatus 10 includes an inner vibrator unit 12 and an outer tampon unit 11 dimensioned to be received in a woman's vaginal canal, and a remote power supply unit 13 disposed outside of the vaginal canal and operatively connected to the inner vibrator unit 12 for the purpose of preventing electrical shocks to the walls of the vaginal canal.

8 Claims, 1 Drawing Sheet

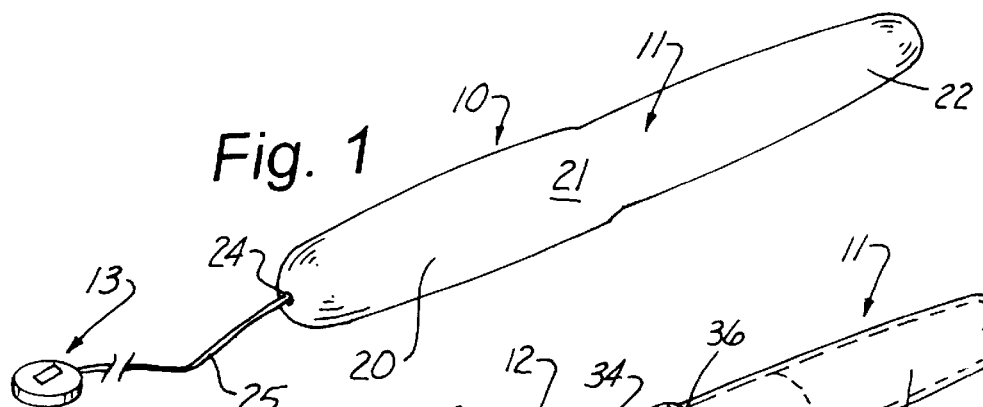
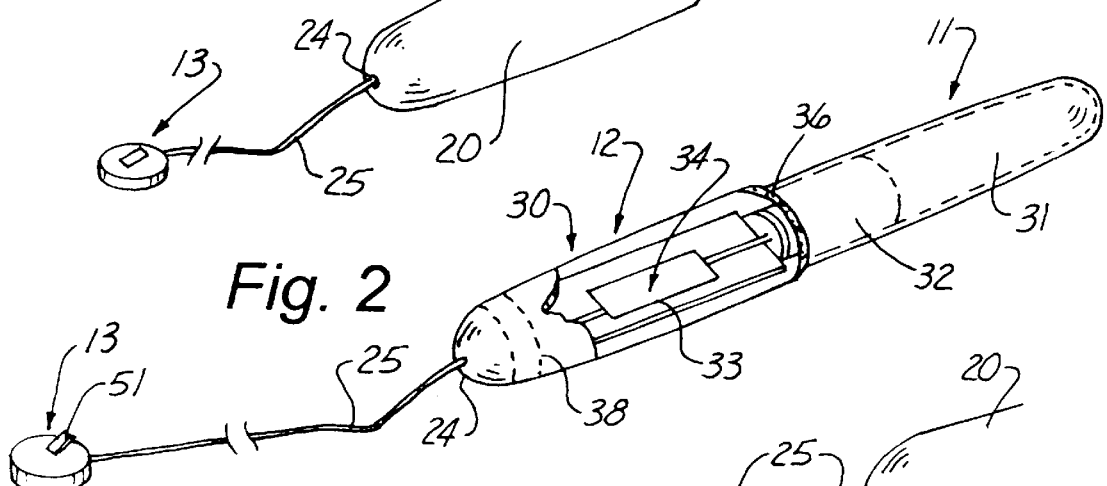
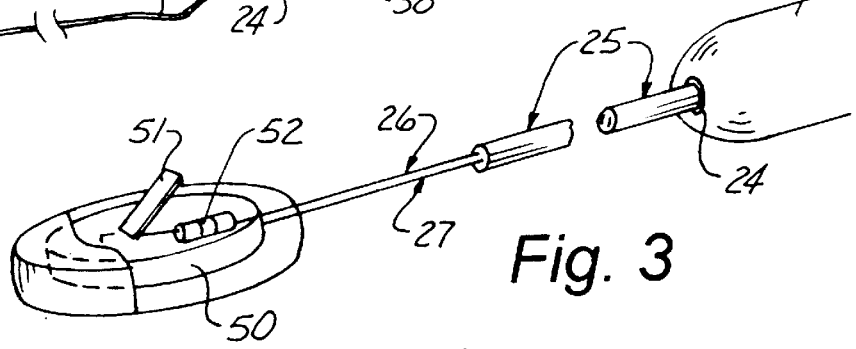
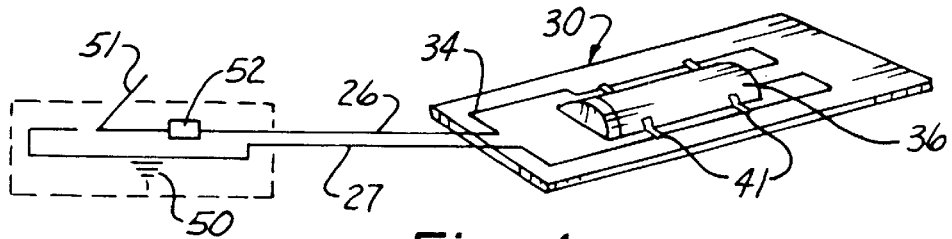
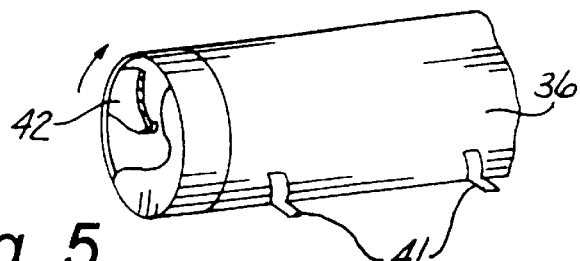

VIBRATING TAMPON APPARATUS

BACKGROUND OF THE INVENTION

1. Field of the Invention

The present invention relates to the field of sanitary napkin constructions in general, and in particular, to a sanitary napkin/tampon construction having a vibrating mechanism incorporated therein and provided with a remote power source.

2. Description of Related Art

This invention is an improvement over my previously patented invention U.S. Pat. No. 5,782,779 which issued on Jul. 21, 1998 and is entitled Vibrating Tampon Apparatus.

As can be seen by reference to the following U.S. Pat. Nos. 2,422,639; 3,626,931; 3,669,100; and 5,067,480, the prior art is replete with myriad and diverse vibrating devices.

While all of the aforementioned prior art constructions are more than adequate for the basic purpose and function for which they have been specifically designed, they are neither designed nor intended to perform the improved dual function that is provided by the subject matter that forms the basis of the present invention.

As many women who suffer menstrual cramps are aware, stimulation of the vaginal tract can, under certain circumstances, alleviate the pain associated with menstrual cramp. In addition, many women experience vaginal dryness at this time which makes the insertion of a tampon a trying experience.

In order to address these needs, U.S. Pat. No. 5,782,779 was developed to provide a self-contained, vibrating mechanism within a tampon wherein the vibrating mechanism was actuated by a string that could also be used to remove the tampon after use.

Subsequent to the development of this invention, it was realized that a very remote possibility existed of an electrical shock being delivered to the user's vaginal walls by virtue of the power source being contained within the body of the tampon.

As a consequence of the foregoing situation, there has existed a need for a new, improved, and safer vibrating tampon construction that not only contains an internal vibrator mechanism wherein the vibrating action will not only facilitate the insertion of the tampon into the vaginal tract and minimize the effects of menstrual cramps but will also perform those functions in a safer manner. The provision of such a construction is a stated objective of the present invention.

BRIEF SUMMARY OF THE INVENTION

Briefly stated, the improved vibrating tampon apparatus that forms the basis of the present invention comprises a tampon with a built-in, vibrating mechanism which may assist a woman by easing menstrual cramps wherein the vibrating mechanism is associated with a remote power source.

The apparatus resembles conventional cotton tampons, including the equivalent of a removal string, but differ greatly on the inside as they contain an internal vibrating motor which is operatively connected to a remote power source. The interior mechanism is housed inside of a nontoxic polyethylene plastic tube which is ultrasonically welded together providing a liquid proof container. This keeps liquids from entering or exiting the interior apparatus.

As will be explained in greater detail further on in the specification, the equivalent of the tampon removal string comprises an insulated pull cable element that encapsulates a pair of electrical leads which operatively connect the remote power source to the internal vibrating motor which is surrounded by the tampon.

In addition, the remote power source includes a low voltage battery member which is electrically coupled to the electrical leads via a switch element; wherein, the positive electrical lead is provided with a micro fuse which prevents a voltage spike being transmitted from the battery member to the vibrator motor which is contained within the vaginal canal.

Furthermore, the low voltage battery member is specifically chosen to have a useful life ranging from an hour or more to as little as twenty minutes depending on the severity of the menstrual cramps being experienced, and the voltage normally required to actuate the vibrator motor for the approximate period of time required to alleviate the situation.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the exterior of the improved vibrating tampon apparatus that forms the basis of this invention.

FIG. 2 is a partial cut-away view showing a portion of the internal vibrating mechanism.

FIG. 3 is a cut-away view of the remote power supply unit.

FIG. 4 is a partial schematic showing the operative connection between the power supply unit and the vibrator member; and FIG. 5 is an isolated detail view of the vibrator motor.

DETAILED DESCRIPTION OF THE INVENTION

As can be seen by reference to the drawings, and in particular to FIG. 1, the vibrating tampon apparatus that forms the basis of the present invention is designated generally by the reference number 10. The apparatus 10 comprises, in general, an outer tampon unit 11, an inner vibrator unit 12, and a remote power supply unit 13. These units will now be described in seriatim fashion.

As can best be seen by reference to FIGS. 1 and 2, the outer tampon unit 11 comprises an elongated tampon member 20 fabricated from a sterile absorbent material 21 such as cotton or the like. The tampon member 20 forms a fabric envelope 22 which surrounds the vibrator unit 12.

In addition, one end 23 of the tampon member 20 is provided with a discrete aperture 24 which is dimensioned to receive a pull cord element 25 whose purpose and function goes beyond that of a conventional tampon string, as will be explained in greater detail further on in the specification.

As shown in FIG. 2, the vibrator unit 12 comprises a generally elongated vibrator member 30 including a male 31 and female 32 casing segment which are joined together in a well recognized fashion to provide a waterproof housing for the internal components of the vibrator member 30.

Turning now to FIGS. 3 through 5, it can be seen that the vibrator member 30 comprises a circuit board 33 having a printed circuit 34 which controls a miniature vibrator motor 36 in response to the output from the remote power supply unit 13.

As shown in FIGS. 2 through 4, the remote power supply unit 13 comprises a low voltage battery member 50 connected by a pair of thin, flexible, electrical leads 26, 27 which are encased within the pull cord element 25 such that the electrical leads 26, 27 can provide electrical current to the vibrator motor 36 from the battery member 50.

As can best be seen by reference to FIGS. 3 and 4, the electrical connection between the battery member 50 and the vibrator motor 36 is further controlled by a switch element 51 which completes the electrical circuit; wherein, a micro fuse 52 is disposed in the positive electrical lead 26 to prevent any power surges from the battery member 50 from being transmitted through the electrical leads 26, 27 to give an electrical shock to a woman employing the apparatus 10.

In addition, the battery member 50 switch element 51 micro fuse 52 and a portion of the electrical leads 26, 27 are contained within an insulated housing element 53 preferably fabricated from soft rubber or plastic to reduce the risk of abrasion by the contact of the power supply unit 13 with the user's skin.

It should also be noted that due to the primary focus of this invention which is to eliminate the possibility that a woman would receive an electrical shock to the vaginal canal and to substantially reduce the possibility of an electrical shock being transmitted to skin surfaces outside of the vaginal canal a great deal of care has been given to the choice of the low voltage battery member 50.

To that end, in the preferred embodiment of the invention, a 2-volt battery member 50 has been found to produce acceptable results. However, it should be noted that the acceptable range of voltages that can be employed in this apparatus can range from a maximum of 3.7 volts to a minimum of 1.5 volts or provide extended operation of the vibrator motor 36.

Turning now to FIGS. 4 and 5, it can be seen that the vibrator motor 36 is secured to the circuit board 33 by a plurality of mounting tabs 41 and one end of the vibrator motor 36 is provided with a motor counterweight 42 whose oscillating motion imparts a vibratory motion to the tampon member 20 via the external case segments 31 and 32.

By now, it should be appreciated that while the present apparatus 10 contains all of the advantages produced by the subject matter of U.S. Pat. No. 5,782,779, it also removes the remote possibility of internal electrical shocks by locating the power source unit 13 at a remote location from the vibrator unit 12 wherein the remote location is positioned at a distance from the vaginal canal as dictated by the length of the pull cord element 25.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An improved vibrating tampon apparatus comprising:
    an inner vibrator member including a vibrator motor contained within a waterproof housing;
    an outer tampon member fabricated from a sterile absorbent material, disposed in a surrounding relationship relative to said inner vibrator member, and dimensioned to be received in a female's vaginal canal; and,
    an remote power source unit electrically connected to said vibrator motor and including a switch coupled with a battery member adapted to be disposed outside of the vaginal canal for providing electrical current to said vibrator motor.

2. The apparatus, as in claim 1; wherein, the outer tampon member is provided with an opening which is dimensioned to receive a pull cord element which is operatively associated with the inner vibrator member.

3. The apparatus as in claim 2; wherein, the pull cord element encapsulates a pair of electrical leads which are operatively connected between the battery member and the vibrator motor.

4. The apparatus as in claim 3; wherein, the pair of electrical leads includes a positive electrical lead provided with a micro-fuse.

5. The apparatus as in claim 4; wherein, the battery member and the micro-fuse are disposed within an insulated housing element.

6. The apparatus as in claim 1; wherein, said battery member has a maximum voltage of 3.7 volts.

7. The apparatus as in claim 1; wherein, said battery member has a minimum voltage of 1.5 volts.

8. The apparatus as in claim 1; wherein, said battery member has a voltage ranging from 3.7 volts to 1.5 volts.

\* \* \* \* \*